(12) United States Patent
Rafat

(10) Patent No.: US 10,568,987 B2
(45) Date of Patent: Feb. 25, 2020

(54) COMPOSITE COLLAGEN HYDROGEL MATERIAL, AN IMPLANTABLE OPTHALMIC DEVICE COMPRISING SUCH MATERIAL AND METHODS OF PRODUCING THE COMPOSITE COLLAGEN HYDROGEL MATERIAL AND THE IMPLANTABLE OPHTHALMIC DEVICE

(71) Applicant: LinkoCare Life Sciences AB, Linköping (SE)

(72) Inventor: Mehrdad Rafat, Linköping (SE)

(73) Assignee: LinkoCare Life Sciences AB, Linköping (SE)

( * ) Notice: Subject to any disclaimer, the term of this patent is extended or adjusted under 35 U.S.C. 154(b) by 0 days.

(21) Appl. No.: 16/003,424

(22) Filed: Jun. 8, 2018

(65) Prior Publication Data
US 2018/0289857 A1    Oct. 11, 2018

Related U.S. Application Data

(63) Continuation of application No. PCT/EP2016/081928, filed on Dec. 20, 2016.

(30) Foreign Application Priority Data

Dec. 22, 2015  (SE) ...................... 1551698

(51) Int. Cl.
| | |
|---|---|
| A61L 27/24 | (2006.01) |
| A61L 27/52 | (2006.01) |
| A61F 2/14 | (2006.01) |
| A61F 2/00 | (2006.01) |
| A61F 2/10 | (2006.01) |
| A61F 2/24 | (2006.01) |
| A61L 27/36 | (2006.01) |
| A61L 27/54 | (2006.01) |
| A61L 27/56 | (2006.01) |

(52) U.S. Cl.
CPC ............ *A61L 27/24* (2013.01); *A61F 2/0063* (2013.01); *A61F 2/105* (2013.01); *A61F 2/142* (2013.01); *A61F 2/1451* (2015.04); *A61F 2/2478* (2013.01); *A61L 27/3675* (2013.01); *A61L 27/52* (2013.01); *A61L 27/54* (2013.01); *A61L 27/56* (2013.01); *A61L 2300/412* (2013.01); *A61L 2300/414* (2013.01); *A61L 2300/64* (2013.01); *A61L 2430/16* (2013.01)

(58) Field of Classification Search
CPC ....................................................... A61L 27/24
See application file for complete search history.

(56) References Cited

U.S. PATENT DOCUMENTS

| | | | | |
|---|---|---|---|---|
| 2006/0134170 | A1* | 6/2006 | Griffith ................ | A61F 9/0017 424/427 |
| 2008/0020012 | A1* | 1/2008 | Ju ........................ | A61L 27/56 424/423 |
| 2008/0269119 | A1* | 10/2008 | Griffith ................ | A61F 9/0017 514/6.9 |
| 2013/0116405 | A1* | 5/2013 | Yu ........................ | A61K 38/10 530/324 |

FOREIGN PATENT DOCUMENTS

| | | |
|---|---|---|
| WO | 2006/015490 A1 | 2/2006 |
| WO | 2009/156866 A2 | 12/2009 |
| WO | 2010/133853 A1 | 11/2010 |

OTHER PUBLICATIONS

Mi et al., 2011, Photochemical cross-linking of plastically compressed collagen gel produces an optimal scaffold for corneal tissue engineering, Journal of Biomedical Materials Research, 99A(1): 8 pages.*
Chai et al., 2013, Nonlinear optical collagen cross-linking and mechanical stiffening: a possible photodynamic therapeutic approach to treating corneal ectasia, Journal of Biomedical Optics, 18(3): 8 pages.*
Xiao et al., 2014, In vivo study of the bioconnpatibility of a novel compressed collagen hydrogel scaffold for artificial corneas, J Biomed Mater Res, 102A: 1782-1787.*
Levis et al., 2012, Plastic Compressed Collagen as a Novel Carrier for Expanded Human Corneal Endothelial Cells for Transplantation, PLoS ONE, 7(11): e50993 (10 pages).*
Mi et al., 2010, Plastic compression of a collagen gel forms a much improved scaffold for ocular surface tissue engineering over conventional collagen gels, J Biomed Mater Res Part A, 95A: 447-453.*
Mi et al. (Wright and Che—eds.), 2013, The Formation of a Tissue-Engineered Cornea Using Plastically Compressed Collagen Scaffolds and Limbal Stem Cells, Corneal Regenerative Medicine: Methods and Protocols, Methods in Molecular Biology, 1014: 143-155.*
Levis et al., 2013, Plastic Compressed Collagen Constructs for Ocular Cell Culture and Transplantation: A New and Improved Technique of Confined Fluid Loss, Current Eye Research, 38: 41-52.*

* cited by examiner

*Primary Examiner* — Amber D Steele
(74) *Attorney, Agent, or Firm* — Marshall, Gerstein & Borun LLP

(57) ABSTRACT

A composite collagen hydrogel material for use in tissue engineering, and an implantable ophthalmic device comprising such composite material. The composite material comprises: a first collagen network comprising collagen crosslinked with a first crosslinking agent, and/or a second collagen network comprising collagen crosslinked with a second crosslinking agent, and a three dimensional collagen mesh comprising partially and plastically compressed collagen hydrogel with a compression degree of 50-95%, wherein the three dimensional collagen mesh is embedded in the first collagen network and/or second collagen network, and the first collagen network and/or the second collagen network and the three dimensional collagen mesh are physically and chemically interconnected in the composite collagen hydrogel material.

18 Claims, 8 Drawing Sheets

COMPOSITE COLLAGEN HYDROGEL MATERIAL, AN IMPLANTABLE OPTHALMIC DEVICE COMPRISING SUCH MATERIAL AND METHODS OF PRODUCING THE COMPOSITE COLLAGEN HYDROGEL MATERIAL AND THE IMPLANTABLE OPHTHALMIC DEVICE

This application is the continuation of International Application No. PCT/EP2016/081928, filed 20 Dec. 2016, which claims the benefit of Swedish Patent Application No. SE 1551698-2, filed 22 Dec. 2015, the entire contents of which are hereby incorporated by reference.

TECHNICAL FIELD

The disclosure is related to a composite collagen hydrogel material for use in tissue engineering and an implantable ophthalmic device comprising such material. The disclosure is also related to methods of producing the composite collagen hydrogel material and the implantable ophthalmic device.

BACKGROUND

Injured and diseased tissues or organs have traditionally been treated or replaced by autologous grafts, allogenic grafts, or synthetic or natural-based biomaterials. However, there is a huge global shortage of tissue grafts. Donor tissue grafts may also cause donor site morbidity and loss of organ functionality and allogenic grafts are associated with the risk of disease transmission and often require the use of immunosuppressant drugs. As for synthetic biomaterials, although many of them have achieved widespread clinical use, seamless integration and immunological response issues still remain. These issues have led to the more recent paradigm shift to the development of tissue-engineered biomaterials and devices that mimic the extracellular matrix (ECM) of the natural tissue for tissue engineering. For these biomaterials to be successful, they need to be mechanically robust and elastic to support and maintain tissue structure, and cell friendly and bio-interactive to allow seamless host-biomaterial integration that helps restore tissue functionality.

The collagens are a family of ECM macromolecules within the body that contribute to both mechanical properties and biological function of various types of tissues such as cornea, skin, bone, tendons, ligaments, blood vessels, and the heart. Although very robust in vivo, extracted collagen is rapidly degraded and lacks the mechanical toughness and elasticity, due to the dissociation of natural cross-links during isolation and purification process.

Present chemical crosslinking techniques often result in collagen-based scaffolds that are either too soft or too brittle, that are not robust enough to resist surgical manipulations or do not actively interact with the body cells and tissues. There is, hence, a need for improved collagen scaffolds that are implantable for tissue engineering and regenerative medicine applications.

In the area of corneal transplant there is an unmet need for an alternative to donor corneas. Prosthetic artificial corneas, cell-based therapies, and scaffold-based therapies have been rigorously pursued but their clinical use has been limited due to challenges including: lack of integration into the surrounding tissue; limited cell sources and functionality; inefficient interaction with host cells and incapability of delivery of therapeutic drugs, respectively. Transplantation of cell-free collagen-based into animal and diseased human corneas have been reported. These scaffolds replace the extracellular matrix or stroma, allowing host cells and nerves to eventually grow over and around the scaffold. However, in blinding conditions of the cornea, such as limbal epithelial stem cell deficiency (LSCD, burn-induced wounds or infection leading to inflammation and neovascularization, use of a stromal scaffold alone (human or tissue-engineered) is insufficient—the underlying stem cell deficiency, inflammation and/or neovascularization must also be addressed to avoid eventual graft failure. For patients with LSCD, transplantation of limbal grafts or ex vivo expanded limbal epithelial stem cells is first required. After limbal restoration, central transplantation (keratoplasty) follows to treat scarring in the visual axis. When corneal scarring is complicated with corneal neovascularization and/or severe infections such as herpes simplex keratitis (HSK), anti-inflammatory, anti-angiogenic, antimicrobial or antiviral agents are administered in conjunction with the standard corticosteroid treatment following (or prior to) the high-risk keratoplasties. These therapeutic regimens are most commonly administered topically with the main challenge of low drug penetration through the corneal epithelium. Limited diffusion across the cornea and the increased washing through the tear drainage result in a low bioavailability of 1-7% for most approved drugs. New administration routes, and ideally a controlled-release drug and cell delivery through biodegradable polymeric implants, would lead to increased success rates of corneal transplantation in these severe inflamed corneas.

In these high-risk applications, bioengineered implants are required not only as transparent and robust scaffolds to replace diseased corneal tissue, but also to deliver therapeutics or stem cells into the cornea. These requirements could be opposing—release of cells or substances requires a degree of bio-degradation, however, this could compromise optical transparency and corneal integrity. Also, requirements of transparency and non-toxicity of biomaterials may complicate the ability to encapsulate, deliver and monitor cells and therapeutic substance release in vivo.

SUMMARY

An object of the present invention is to provide a composite collagen hydrogel material for use in tissue engineering overcoming or at least alleviating some of the disadvantages with known collagen scaffolds. Other objectives are to provide an implantable ophthalmic device comprising such a composite collagen hydrogel material and to provide methods of producing the composite collagen hydrogel material and the implantable ophthalmic device.

The invention is defined by the appended independent claims. Embodiments are set forth in the appended dependent claims and in the figures.

According to a first aspect, there is provided a composite collagen hydrogel material for use in tissue engineering, comprising a first collagen network comprising collagen crosslinked with a first crosslinking agent, and/or a second collagen network comprising collagen crosslinked with a second crosslinking agent, and a three dimensional collagen mesh comprising partially and plastically compressed collagen hydrogel with a compression degree of 50-95%, wherein the three dimensional collagen mesh is embedded in the first collagen network and/or second collagen network, and the first collagen network and/or the second collagen network and the three dimensional collagen mesh are physically and chemically interconnected in the composite collagen hydrogel material.

The first collagen network and/or the second collagen network and the three dimensional collagen mesh are physically interconnected through penetration of crosslinked network(s) into the three dimensional collagen mesh and also chemically crosslinked via covalent bonds between collagen fibrils in the crosslinked collagen network(s) and fibrils in the three dimensional collagen mesh. The constituents of the composite material, i.e. the first crosslinked collagen network and/or the second crosslinked collagen network and the three dimensional collagen mesh form a merged composite material without distinct interfaces between the constituents.

There is a smooth transition between the constituents of the material, creating a homogenous appearance. In other words, no distinct phase interface is discernible between the constituents in the composite material.

When viewing a cross-sectional side-view of the composite collagen hydrogel material, the embedded three dimensional collagen mesh may be centrally located or off-centrally located, i.e. located closer to a surface of the composite material.

The composite material could comprise a first crosslinked collagen network and the three dimensional collagen mesh, the second crosslinked collagen network and the three dimensional collagen mesh or the first crosslinked collagen network, the second crosslinked collagen network and the three dimensional collagen mesh.

The first and second crosslinking agent may be the same crosslinking agent. Alternatively, the first and second crosslinking agent may be different crosslinking agents.

With "hydrogel material" is here meant a collagen network which exhibits the ability to swell in water or aqueous solution without dissolution, retaining a significant portion of water or aqueous solution within its structure.

With "three dimensional collagen mesh" is here meant a three dimensional (non-crosslinked) collagen mesh network.

In the crosslinked first and second collagen networks intra- and inter chain bridges between/within collagen molecules and fibrils are formed. These crosslinks and the interlinks between the three dimensional mesh and the first and/or second crosslinked collagen network made it achievable to simultaneously enhance mechanical strength, and elasticity while retaining biological characteristics (cell friendly and non-toxic in vitro and in vivo). The new composite collagen hydrogel material is, hence, biocompatible, strong, elastic, hold sutures and therefore implantable.

By varying the degree of crosslinking of the first and/or second collagen network and the content of collagen in the crosslinked collagen network(s) and the three dimensional collagen mesh, the porosity of the composite material and the degradation rate of the material can be tuned.

With a three dimensional collagen mesh comprising partially and plastically compressed collagen hydrogel with a compression degree of 50-95% is here meant that collagen hydrogel (without any crosslinking agent) has been subject to a mechanical compressive force/stress to expel interstitial fluid from the hydrogel. Such fluid is not part of the collagen structure but is a result of the casting of the hydrogel, i.e. collagen gel is formed by, for example, incubating a collagen solution in an elevated temperature (such as 37° C.). Collagen monomers then polymerize to fibrils. There is phase transition and a semi-solid network of fibrils formed supporting the remaining interstitial liquid resulting in gel formation.

Controlled compaction, compressive stress, may be applied to the top and/or bottom surfaces of the hydrogel expelling interstitial fluid from the gel such that the gel height/volume is reduced by 50-95%, forming the three dimensional collagen mesh.

In one non-limiting example the height of the gel before plastic compression is 1000 μm and after compression 100 μm, i.e. a compression degree of 90%.

The collagen gel before compression comprises fibrils in an interstitial liquid. The collagen gel is isotropic and the collagen fibers randomly oriented.

Through plastic compression of the hydrogel the gel is deformed to reduce its height/volume, such that the gel retains or substantially retains its new height/volume after the cause of compaction is removed. Plastic compression of a collagen gel reduces the distance between collagen fibrils and increases the number of contact points between adjacent fibrils in the hydrogel, forming a three dimensional mesh hydrogel.

With a low compression degree (e.g. a volume/height reduction of 50%), the hydrogel has a tissue-like overall collagen density but the lamella structure is increasingly poorly defined as the compression degree decreases, i.e. everything gets bonded together to similar extent and variation across the compression axis becomes smaller and smaller over the same length scale.

With a high compression degree (e.g. a volume/height reduction of 95%), there is greater structural heterogeneity across the compression axis and a gradient is created of interstitial fluid with lowest concentration at the surface of compression.

If the three dimensional mesh is fully compressed, i.e. close to a compression degree of 100%, it will not be porous enough to allow penetration of the first and second crosslinked networks resulting in a two dimensional brittle mesh.

Partial compression (volume reduction of 50-95%) of the hydrogel produces denser three dimensional collagen mesh networks with more tissue-like architecture and stronger mechanical properties than non-compressed and non-crosslinked collagen hydrogels.

The three dimensional mesh produced by partial compression is more elastic than the one produced by full compression.

The compression level may be adjusted to obtain a specific degradation rate in vitro and in vivo. The higher the compression level the slower is the degradation rate of the mesh.

The compression speed should be slow enough (e.g. 10 mm/s) to prevent collagen fibrilization (premature fibril formation and precipitating out of the solution) and fast enough to prevent hydrogel drying.

The three dimensional collagen mesh acts as a supporting network embedded and merged with the first and or second network(s), minimizing premature tears or breakage of the scaffold when subjected to external forces such as suturing.

One of the main advantages of the composite collagen hydrogel material described above compared to existing bioengineered scaffolds is that it has multiple functionalities and meet essential requirements such as cell and therapeutics delivery and scaffold integrity that are most often opposing. For example, in the high-risk applications and patients, bioengineered implants are required not only as robust scaffolds to replace diseased tissue, but also to deliver therapeutics or stem cells into the surrounding tissue. For instance, release of cells or substances requires a degree of bio-degradation, however, this could compromise other properties such as optical transparency and tissue integrity. Also, requirements of transparency and non-toxicity of biomaterials may complicate the ability to encapsulate, deliver and monitor cells and therapeutic substance release in vivo.

The partially and plastically compressed collagen hydrogel may have a compression degree of 55-90%, preferably 60-85%.

For the same initial collagen concentrations, the higher compression degree (the more fluid removed) the more dense and less porous the three dimensional collagen mesh becomes. This may result in a brittle three dimensional collagen mesh and may prevent the penetration of the first and or second collagen networks into the three dimensional collagen mesh. This may reduce the homogeneity of the composite material and decrease the mechanical robustness and suturability characteristics of the material.

The collagen of the first and/or second network and the three dimensional collagen mesh may be selected from a group consisting of Type I collagen, Type II collagen, Type III collagen, Type IV collagen, Type V collagen, Type VI collagen, and denatured collagen from animal sources and human recombinant collagens.

The first and/or second collagen network and the three dimensional collagen mesh may comprise the same type of collagen.

This results in a good materials' match among different constituents. This phenomenon eliminates materials' mismatch and enhances homogeneity, and spreading of the structural components holding different forms of collagen together resulting in an enhanced load distribution and handling during implantation.

In one non-limiting example the crosslinked collagen network(s) and the three dimensional collagen mesh comprises collagen Type I.

The collagen content in the first and/or second collagen network may be 1-50%, preferably 10-20%.

A wide range of collagen concentration provides a tool for modulating scaffold properties such as mechanical strength, biodegradability, porosity and permeability toward nutrients and metabolites and cell interaction.

The first and/or second crosslinking agent may be a non-polymeric short-range carboddimide crosslinking agent selected from a group comprising Ethyl-N'-(3-dimethylaminopropyl) carbodiimide hydrochloride (EDAC), 1-[3-(dimethylamino)propyl]-3-ethylcarbodiimide methiodide (EDCM), dicyclohexyl-carbodiimide (DCC), N-hydroxy-succinimide (NHS) and combinations thereof.

The first and/or second crosslinking agent may be a polymeric long-range amine-type multi-functional crosslinking agent comprising amine-type multifunctional crosslinkers from the polyethylene glycol (PEG) family, selected from a group comprising PEG Succinimidyl ester (NHS-PEG-NHS) Multi-arm PEG Succinimidyl NHS ester, poly (ethylene glycol) dialdehyde (PEG-DA), polyethylene glycol dibutylaldehyde, polyethylene glycol diacrylate and combinations thereof.

When two crosslinked collagen networks are used, the first crosslinking agent may be a short range carbodiimide crosslinking agent and the second crosslinking agent may be a polymeric long-range crosslinking agent.

The crosslinking agents of the two crosslinked networks should preferably be different. The combination of short range and long range crosslinkers results in synergistic effects on mechanical strength and elasticity. Short-range cross-links connect collagen fibrils that are in each others vicinity to enhance scaffold's strength, which may reduce the elasticity, while long-range crosslinks connect collagen fibrils that are in further distance from each other, which enhances intermolecular/interfibrilar cross-links resulting in significantly enhanced robustness and elasticity simultaneously.

The pH of the first and/or second collagen networks may be acidic, pH 3-6, and the pH of the three dimensional collagen mesh may be neutral, about pH 7.

pH plays a key role in the crosslinking efficiency and therefore a is tool to control degradation gradient within the composite collagen hydrogel material.

pH-gradients may be formed in the composite material with the highest pH in the center of the three dimensional collagen mesh.

A molar ratio of the first crosslinked collagen network to the second crosslinked collagen network in the composite collagen hydrogel material may be 1:1 to 1:5, or 1:1 to 100:1.

The wide range of crosslinkers ratios provides a good design tool for customizing the scaffolds' characteristics.

The molar ratio of the first crosslinking agent to collagen in the first crosslinked collagen network may be 0.5:1 to 3:1, preferably 1:1.

The crosslinking degree is dependent on the ratio of collagen to crosslinking agent.

The molar ratio of the second crosslinking agent to collagen in the second crosslinked collagen network may be 0.1:1 to 2:1, preferably 0.5:1.

The collagen content of the three dimensional collagen mesh may be 0.1-20%, preferably 0.5-10% or 1-5%.

A lower collagen content in the three dimensional collagen mesh may result in a less stable three dimensional collagen mesh and, hence, less stable composite material.

The ratio of the collagen content in the three dimensional collagen mesh to the collagen content in the first and/or second collagen network may be 1:50, preferably 1:40 or 1:30.

The three dimensional collagen mesh may be loadable with cells, tissue factors, growth factors, bioactive agents and drugs.

The three dimensional collagen mesh may be impregnated with viable cells prior to compression, so that the cells are contained within the collagen gel. The compression degree may be adapted to minimize cell damage.

The three dimensional collagen mesh may be essentially transparent having a light transmission of more than 80%, essentially translucent having a light transmission of more than 20% and less than 80%, or essentially opaque having a light transmission of less than 20%.

The composite described above may be for use in ophthalmic devices, skin replacement, cardiac wall repairs or cardiac patch applications, or repair of weak abdominal wall.

The repair of weak abdominal wall may for example be repair of a hernia.

According to a second aspect there is provided an implantable ophthalmic device comprising a first and a second region, wherein the first region comprises the composite collagen hydrogel material described above, and the second region comprises an essentially transparent crosslinked collagen hydrogel comprising the same first and/or second crosslinked collagen networks as the composite hydrogel material, wherein the first and second regions are interconnected regions connected through the first and/or second crosslinked collagen networks.

With essentially transparent crosslinked collagen hydrogel is here meant that the there is at least 80% transmission of white light through the first portion of the ophthalmic device and less than 10% light scatter.

That the first and second regions are interconnected regions connected through the first and/or second crosslinked collagen networks is here meant that there is a smooth transition between adjacent first and second regions of the device due to the presence of the same crosslinked collagen network(s) in both regions.

The second region may restore corneal transparency while the first region may serve as a reservoir for cells and drugs to ensure survival of an implanted device.

Tear and breakage at the interface between the first and second region may be low due to the homogeneity between first and second regions, i.e. the first and second region contain the same crosslinked collagen network(s).

The first region may smoothly distribute mechanical loads and shear stress due to for example suturing and mechanical forces exerted on the device.

The implantable ophthalmic device is a device which is elastic and suturable, due to the presence of the first region. The first region may hold sutures better than the second region as it is possible to make more elastic than the second region, due to the presence of the three dimensional collagen mesh.

The implantable ophthalmic device may be more mechanically robust than prior art ophthalmic implants without first and second regions, which only comprise a region corresponding to the second region of the present device. The first region smoothly distributes mechanical loads and shear stress due to suturing and post-surgical mechanical forces caused by blinking or external trauma.

The first region may be loaded with cells, tissue factors, growth factors, bioactive agents and drugs which may be delivered to the area of implantation improving and increasing tissue regeneration. The first region may also recruit host stromal cells locking the device in place, while the second region has a maintained integrity and transparency. To induce tissue regeneration, the triad of tissue engineering (biomaterials, cells, and signaling molecules such as growth factors and therapeutic drugs) must be present. This new scaffold design fulfills this crucial requirement.

The combinations of short range and long range crosslinks and the mesh-hydrogel interlinks made it achievable to simultaneously enhance mechanical strength, and elasticity while retaining biological characteristics (cell friendly and non-toxic in vitro and in vivo) and not compromising the optical clarity in the second region. The new scaffold is biocompatible, strong, elastic, hold sutures and therefore implantable by penetrating keratoplasty, and superior to human eye bank corneas in optical clarity.

pH-gradients may be formed in the composite material with the highest pH in the center of the three dimensional collagen mesh and the lowest pH at the center of the non-mesh region.

Prior art cell-free collagen-based corneal scaffolds allow host cells and nerves to eventually grow over and around the scaffold. However, in blinding conditions of the cornea, such as limbal epithelial stem cell deficiency (LSCD), burn-induced wounds or infection leading to inflammation and neovascularization, use of a stromal scaffold alone is insufficient—the underlying stem cell deficiency, inflammation and/or neovascularization must also be addressed to avoid eventual graft failure. For patients with LSCD, transplantation of limbal grafts or ex vivo expanded limbal epithelial stem cells is first required. After limbal restoration, central transplantation (keratoplasty) follows to treat scarring in the visual axis. When corneal scarring is complicated with corneal neovascularization and/or severe infections such as herpes simplex keratitis (HSK), anti-inflammatory, anti-angiogenic, antimicrobial or antiviral agents are administered in conjunction with the standard corticosteroid treatment following (or prior to) the high-risk keratoplasties. These therapeutic regimens are most commonly administered topically with the main challenge of low drug penetration through the corneal epithelium. Limited diffusion across the cornea and the increased washing through the tear drainage result in a low bioavailability of 1-7% for most approved drugs. New administration routes, and ideally a controlled-release drug and cell delivery through biodegradable polymeric implants, would lead to increased success rates of corneal transplantation in these severe inflamed corneas.

In these high-risk applications, bioengineered implants are required not only as transparent and robust scaffolds to replace diseased corneal tissue, but also to deliver therapeutics or stem cells into the cornea. These requirements could be opposing—release of cells or substances requires a degree of bio-degradation, however, this could compromise optical transparency and corneal integrity. Also, requirements of transparency and non-toxicity of biomaterials may complicate the ability to encapsulate, deliver and monitor cells and therapeutic substance release in vivo.

The implantable ophthalmic device described above, hence, is a solution to this problem as the second region of the device may function as a corneal stromal substitute and the first region as a biodegradable reservoir for therapeutic drugs and cells. The second region being transparent and stably cross-linked collagen hydrogel and the first region a mechanically compressed three dimensional collagen mesh embedded in the crosslinked collagen network of the second region.

This design allows the first region to degrade faster than the second region, therefore renders the composite slow cell/drug release ability.

The collagen content, crosslinking degree and crosslinking agent of the first and/or second crosslinked collagen networks of the first and second region may be the same. The first and second regions may have different degradation rate in vitro as measured by collagenase degradation, wherein the first region may degrade 2-100 times faster than the second region.

The first and second regions may have different degradation rate in vivo, wherein the first region may degrade 2-100 times faster than the second region. Degradation rate in vivo may be tracked by tracing the visible opaque mesh within the implanted ophthalmic device.

The degradation gradient in the first and second regions may be created to facilitate encapsulation and release of cells and therapeutic agents in the first region while maintaining a stable scaffold in the second region as a tissue replacement and mechanical support for the surrounding tissues. The ascending degradation rate gradient from the second region toward the first region may be achieved by using collagens in different forms, at different acidities, and at different crosslinking ratios in the first and second regions.

The implantable ophthalmic device may be a corneal onlay, corneal inlay, or full-thickness corneal implant.

A "corneal onlay" is here an ophthalmic device configured, in size and shape, to be located between the epithelium or an epithelial cell layer and the Bowman's membrane in an eye, of a human or animal. A corneal onlay may rest entirely over the Bowman's membrane, or it may include one or more portions that extend into Bowman's membrane.

A "corneal inlay" is a device or implant configured to be placed in the stroma of an eye. Corneal inlays may be placed in the stroma by forming a flap or a pocket in the stroma. Corneal inlays are placed below the Bowman's membrane of an eye.

A "full-thickness corneal implant" refers to a device that is configured to replace all or part of an unhealthy cornea of an eye located anterior to the aqueous humour of the eye.

The first region may be positioned in a peripheral area of the device. It may be seen as a skirt area. In the corneal application the second region may be a central region and the first region a peripheral, skirt region, surrounding the second region.

The first region may hold sutures better than the second region.

According to a third aspect there is provided a method of producing a composite collagen hydrogel material, comprising the steps of: forming a first collagen network in liquid form, the collagen network comprising collagen crosslinked with a first crosslinking agent, and/or forming a second collagen network in liquid form, the collagen network comprising collagen crosslinked with a second crosslinking agent, forming a three dimensional collagen mesh by partial plastic compression of a collagen hydrogel to a compression degree of 50-95%, and simultaneous compression molding of the first collagen network and/or the second collagen network and the three dimensional collagen mesh to form a physically and chemically interconnected composite collagen hydrogel material, wherein the three dimensional collagen mesh is embedded in the first collagen network and/or second collagen network.

With simultaneous is here meant that all networks are formed at the same time.

The first region may be essentially transparent having a light transmission of more than 80%, essentially translucent having a light transmission of more than 20% and less than 80%, or essentially opaque having a light transmission of less than 20%.

If the first region is non-transparent but at least partially opaque it may be possible to track an implanted device in vivo and non-invasively.

According to a fourth aspect there is provided a method of producing an implantable ophthalmic device, comprising the steps of: forming a first collagen network in liquid form, the collagen network comprising collagen crosslinked with a first crosslinking agent, and/or forming a second collagen network in liquid form, the collagen network comprising collagen crosslinked with a second crosslinking agent, forming a three dimensional collagen mesh by plastic compression of a collagen hydrogel to a compression degree of 50-95%, removing area(s) of material from the formed three dimensional collagen mesh, and simultaneous compression molding of the first collagen network and/or the second collagen network and the three dimensional collagen mesh with the removed area(s) to form an implantable ophthalmic device comprising a first region comprising physically and chemically interconnected composite collagen hydrogel material, wherein the three dimensional collagen mesh is embedded in the first crosslinked collagen network and/or the second crosslinked collagen network, and (a) second mesh free region(s), corresponding to the removed area(s) of the three dimensional collagen mesh, comprising essentially transparent crosslinked collagen hydrogel comprising the first and/or second crosslinked collagen networks.

Removing area(s) of material from the formed three dimensional collagen mesh may here mean forming a three dimensional mesh ring.

Such three dimensional collagen mesh ring may have a removed area, i.e. a mesh free hole, as the central optic of an implantable core-and-skirt ophthalmic device, the skirt comprising composite collagen hydrogel material and the core essentially transparent crosslinked collagen network.

DETAILED DESCRIPTION

Figure 1:
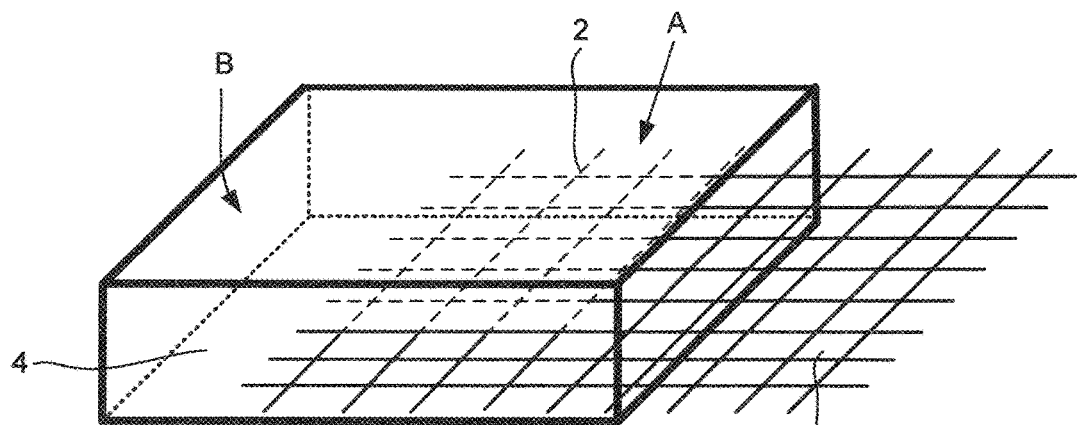
FIG. 1 is a schematic view of a device comprising a composite collagen hydrogel material in a first region of the device and in a second region an essentially transparent crosslinked collagen hydrogel.

In FIG. 1 is shown a schematic view of a device 1 comprising a first region A with a composite collagen hydrogel material 2 comprising a partially compressed three dimensional collagen mesh 3 embedded in a crosslinked collagen network 4 and a second region B comprising the crosslinked collagen network 3 only.

Figure 2A:
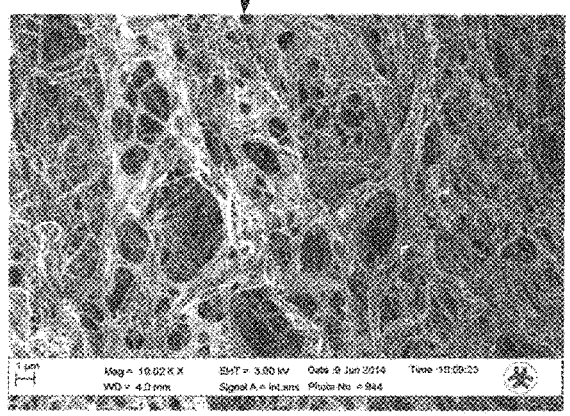
FIGS. 2a-2c are Scanning Electron Microscopy (SEM) micrographs of different regions of the device in FIG. 1.
Figure 2B:
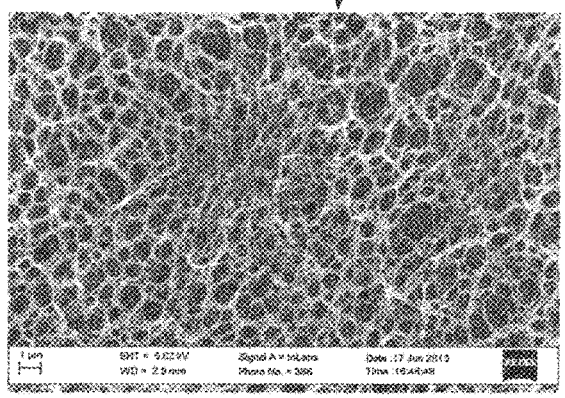
Figure 2C:
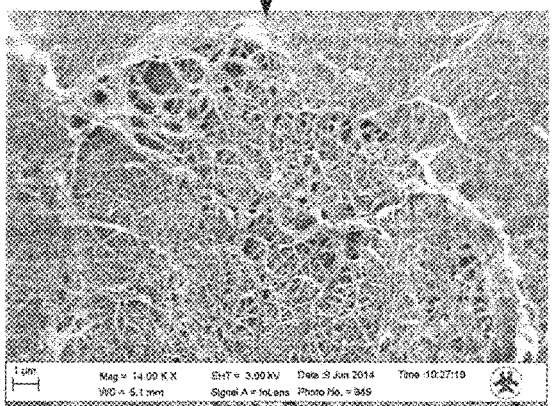

The Scanning Electron Microscopy (SEM) micrograph in FIG. 2a shows a SEM micrograph of the three dimensional collagen mesh 3 before being merged into the crosslinked collagen network 4. In FIG. 2b the crosslinked collagen network 4 of region B of the device 1 is shown while FIG. 2c shows a SEM micrograph of the composite collagen hydrogel material 2 in the first region A. As can be seen in these micrographs the three dimensional collagen mesh 3 (FIG. 2a) exhibits a more compact fibrous structure compared to the crosslinked collagen network 4 (FIG. 2b).

Figure 3:
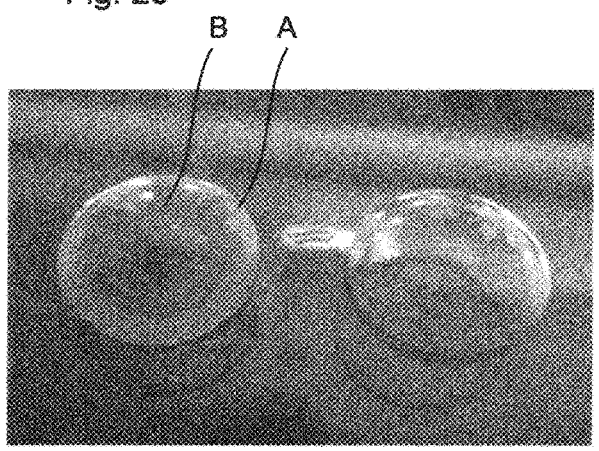
FIG. 3 shows an implantable ophthalmic device, corneal implant, with a peripheral first region that is opaque and visible and a second transparent region.

In FIG. 3 is shown an implantable ophthalmic device, corneal implant, with a first peripheral opaque region A and a second transparent region B.

Figure 4:
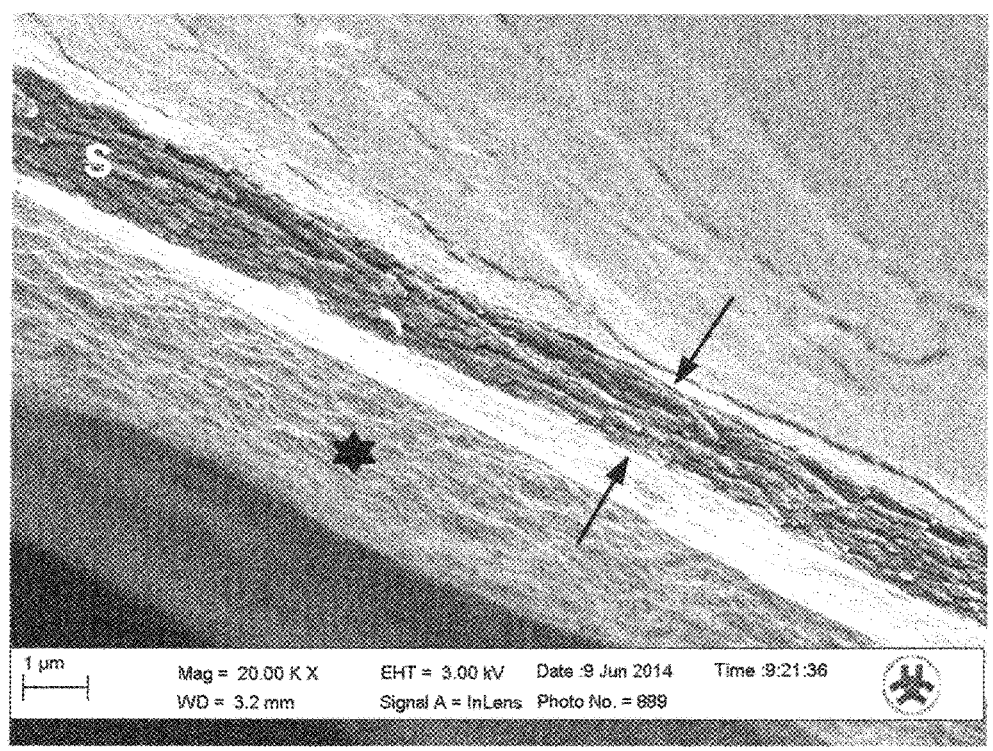
FIG. 4 shows a scanning electron micrograph of the device in FIG. 1.

In FIG. 4 is shown a scanning electron micrograph of the first region A, marked S in the micrograph, and the second region B, marked with a star in the micrograph. The arrows in the micrograph indicate the cross-section of the first region A exhibiting a more fibrous structure compared to the second region B.

Microstructural analysis of the device 1 by electron microscopy revealed that collagen fibers in the first region A formed a more fibrous structure with a degree of localized self-alignment whereas the second region B had a more uniform, but less densely-packed fibril distribution. The fiber diameter in the first region A was significantly thinner ($P<0.001$) than in the second region and in the native rabbit stroma, see FIG. 5.

In the following experimental and characterization section the production methods of the device 1 described above and the composite collagen hydrogel material are described. Special focus is on implantable ophthalmic devices comprising such composite materials. As discussed above, the composite hydrogel material is, however, also suitable as tissue equivalents for replacement of other tissues and may be used as skin replacement, as a cardiac patch to repair the cardiac wall or for the repair of weak abdominal wall.

EXPERIMENTAL

Chemicals

Crosslinking agents: 1-[3-(Dimethylamino)propyl]-3-ethylcarbodiimide methiodide (EDCM) and N-hydroxysuccinimide (NHS), Poly(ethylene glycol) dialdehyde (PEG-DA, $M_n$=2000); collagen (atelo type-I) obtained and highly purified from *porcine* skin.

Crosslinked Collagen Network

Dilute solutions (0.1%) of collagen were lyophilized under controlled conditions and then reconstituted in sterile water to make a target collagen concentration of e.g. 18%. The high collagen concentration can also be achieved by controlled vacuum evaporation of the dilute solution at room temperature. The collagen solutions were centrifuged and transferred into separate glass syringes. The pH of the solutions were adjusted to 3-6. Predetermined amounts of the crosslinking agents EDCM/NHS and poly(ethylene glycol) dialdehyde (PEG-DA) were separately dissolved in water at a 18% w/w concentration and added to each collagen solution at 0.75:1 and 0.5:1 molar ratios for the first crosslinking agent and the second crosslinking agent to collagen respectively, while mixing thoroughly. The ratio of first crosslinked collagen network to second crosslinked collagen network was 1:0.5. The separate solutions were then mixed together in a syringe system and thereafter molded between glass plates or in curved corneal molds to make a homogeneous hydrogel scaffold. A 150 µm thick spacer and a clamping system were used for compression molding of 150 µm thick scaffolds. Samples were cured at 37° C., in 90% humidity chambers. De-molding was achieved by immersion in phosphate buffered saline (PBS) for 1 hour. Samples were subsequently washed three times with PBS solution (1× PBS, containing 1% v/v chloroform) at room temperature to extract reaction byproducts, and to sanitize the samples.

Alternatively, only one crosslinking agent may be used for forming the crosslinked collagen network.

Composite Collagen Hydrogel Material

Figure 6:
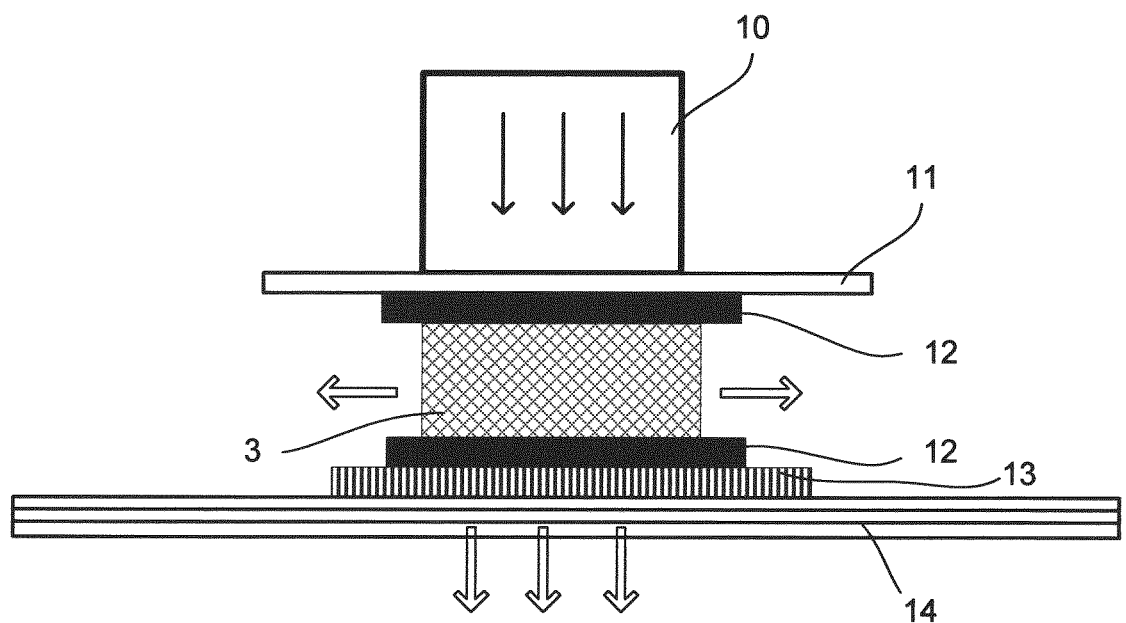
FIG. 6 illustrates plastic compression of the mesh hydrogel.

1% and 2% solutions of collagen type I were made and then mixed with 1× Dulbecco's Modified Eagle Medium (DMEM) at 9:1 ratio. After adjusting the pH to neutral pH, about 7, and incubation at 37° C., the hydrogel solution was partially compressed to form the three dimensional collagen mesh 3. In FIG. 6 the plastic compression procedure is illustrated. The hydrogel solution 3 was placed between two plastic meshes 12. On top of the upper plastic mesh is placed a glass plate 11 and below the lower plastic mesh 12 is placed a wire mesh 13 and filter paper 14. On top of the glass plate a load 10 is applied in the direction of the arrows to partially remove interstitial fluid from the hydrogel (fluid exits the hydrogel as indicate by the arrows in FIG. 6) to form a three dimensional collagen mesh. Two thicknesses of the three dimensional collagen meshes were fabricated. Collagen concentrations of 1% and 2% were used for a first and second three dimensional collagen mesh. The first mesh had a compression degree of 95% (height of the gel was reduced from 1000 µm to 50 µm). The second mesh had a compression degree of 90% (height of the gel was reduced from 1000 µm to 100 µm).

Thick or thin collagen meshes were then set within a collagen crosslinker mixture comprising a) 18% collagen solution and the crosslinking agents EDCM/NHS and/or b) poly(ethylene glycol) dialdehyde (PEG-DA), at the ratio of the collagen content in the collagen mesh network to the collagen content in the first and/or second collagen network is 1:40. The other ratios and pH were the same as the ones described for crosslinked collagen network. The whole combination was thereafter molded and sandwiched between two glass plates with 150 µm spacers and compressed to make a homogeneous composite collagen hydrogel. Compression molding allowed the collagen-crosslinker mixture to penetrate into the partially compressed collagen mesh forming a single merged mesh-hydrogel composite. The composite was cured at 37° C. for 24 hours, then demolded and washed in PBS. Transparency depended on collagen concentration and compression degree in the three dimensional collagen mesh, with the 2% solution resulting in more opacity than 1%.

Implantable Ophthalmic Devices

Figure 7:
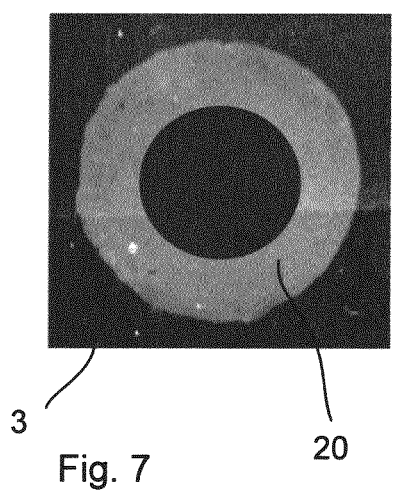
FIG. 7 shows a collagen mesh with a centrally removed section.

Implantable ophthalmic devices were fabricated as the composite collagen hydrogel material above. Buttons 20 (2-7 mm dia.) were removed from the partially compressed mesh 3, see FIG. 7. The collagen mesh was then set within a collagen crosslinker mixture in between the glass plates or within curved corneal molds and further compressed as above forming a single merged mesh-hydrogel composite with mesh-free regions corresponding to the areas with removed buttons which become occupied by the crosslinked collagen.

Control

As a negative control for cell culture and mechanical tests, polypropylene mesh (BD Biosciences, San Jose, USA) was used instead of collagen mesh to form a fully synthetic mesh, which was subsequently embedded in a crosslinked solution, following the above procedure.

Characterization

Light Transmission and Scatter Measurements

Light transmission and scatter were measured at room temperature, with white light (quartz-halogen lamp source) and narrow spectral regions (centered at 450, 550, and 650 nm) using a custom-built optical instrument. 150 µm-thick samples were hydrated in PBS before and during measurements.

Figure 8A:
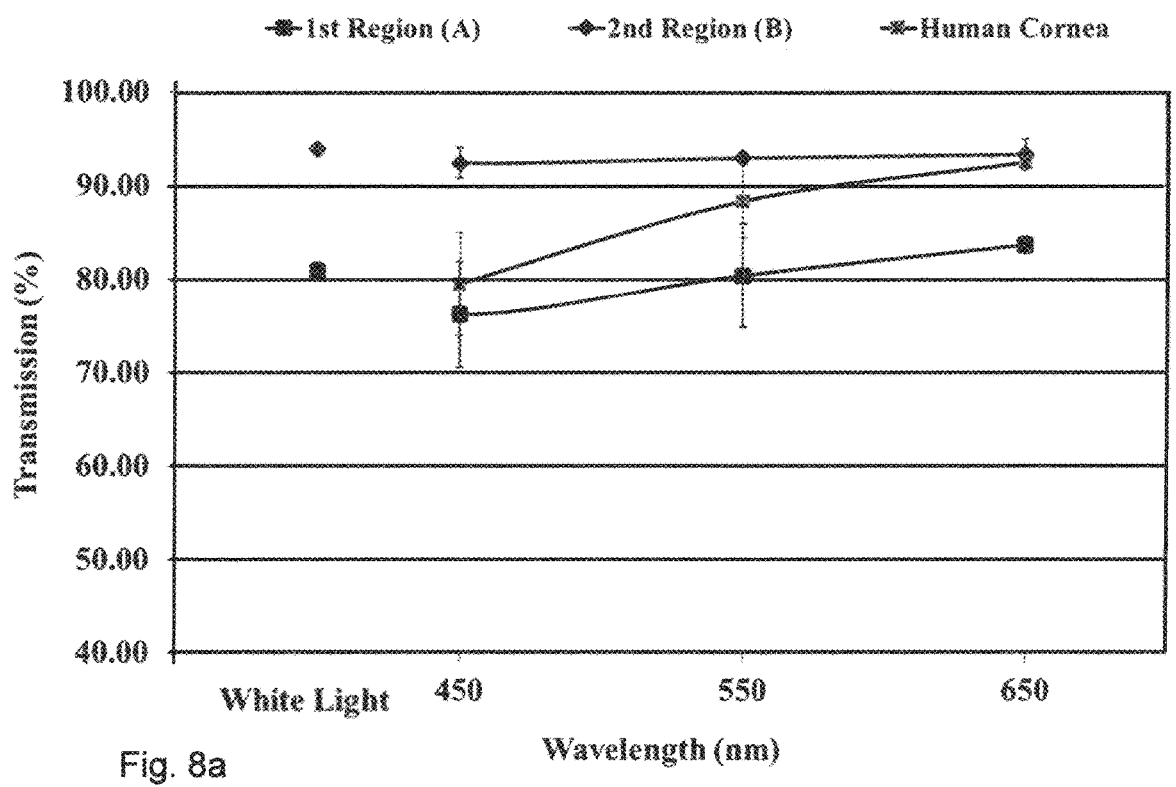
FIGS. 8a and 8b show light transmission and light scatter for different materials.
Figure 8B:
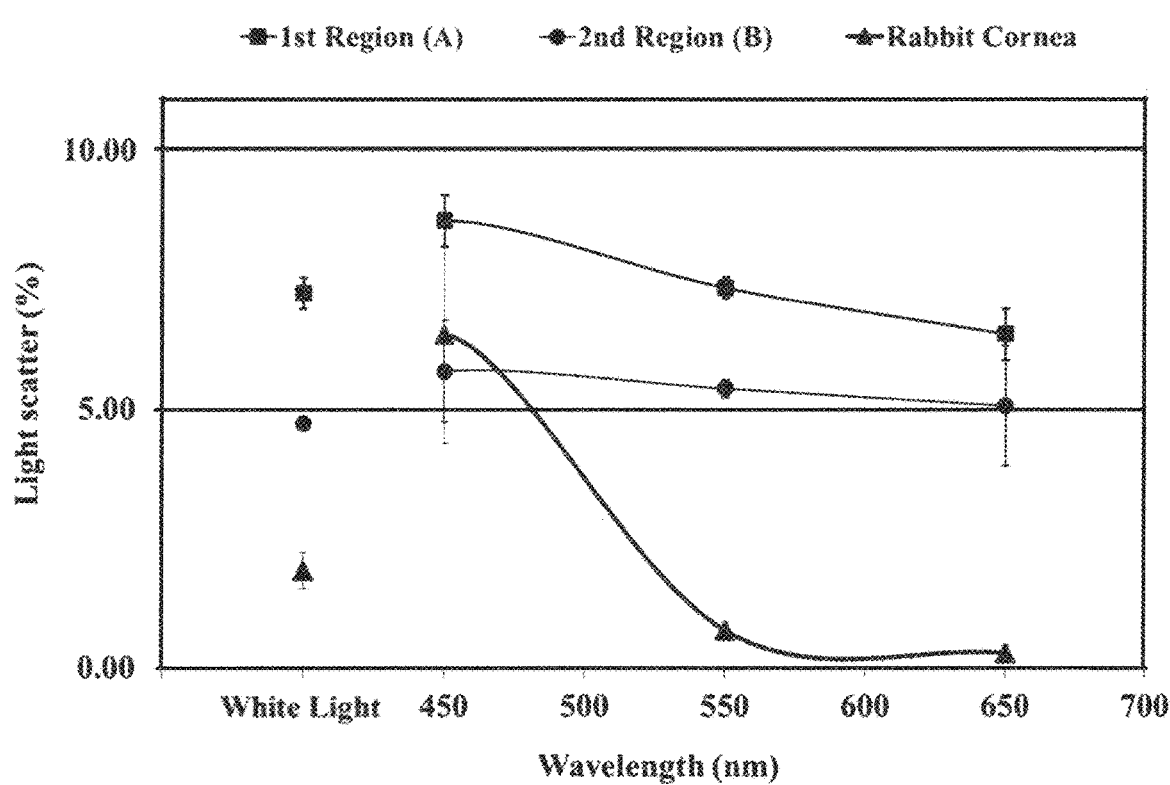

Human cornea, native rabbit cornea, crosslinked collagen network 4 and composite collagen hydrogel material 2 were evaluated. Control of collagen mesh transparency in the composite material was achieved by varying the collagen concentration between 1-2% and the mesh thickness from 50-100 µm. Light transmission and scatter, see FIG. 8a, indicated that the crosslinked collagen network 4 had superior light transmission to human donor cornea, while transmission was controllably reduced in the composite material 2 compared to the crosslinked collagen network 4 and the human donor cornea. Reduced transmission and increased scatter, see FIG. 8b, were due to additional compressed collagen fibers in the composite material 2, which may be used to facilitate in vivo tracking of implant degradation. The percent light scatter of crosslinked collagen network 4 was elevated (4-5% scatter) relative to the native rabbit cornea (1-2%) but still below the transparency threshold of 10%. The percent light scatter for the composite material 2 was higher than those for the crosslinked collagen network 4 and the rabbit which was due to the highly packed collagen fibers.

Mechanical Properties

The impact of collagen mesh 3 incorporation into crosslinked collagen network 4 on mechanical properties was evaluated using an Instron Series IX Automated Materials Testing System (Model 3343, Instron, Canton, Mass.) equipped with a load cell of 50N capacity and pneumatic metal grips at a crosshead speed of 5 mm/min. Collagen solutions were dispensed and cured in dumbbell-shaped Teflon molds, with ends containing collagen mesh and center remaining mesh-free. A synthetic mesh made from polypropylene (PP) mesh was also incorporated into the ends of some samples for comparison with the collagen-based mesh and to investigate the impact of materials match/mismatch on mechanical behavior of the composite materials. PBS-equilibrated dumbbell specimens were attached to the grips with a pneumatic pressure of 40 psi and immersed in a temperature-controlled container (BioPuls bath) filled with PBS at 37° C. during the test.

Figure 9A:
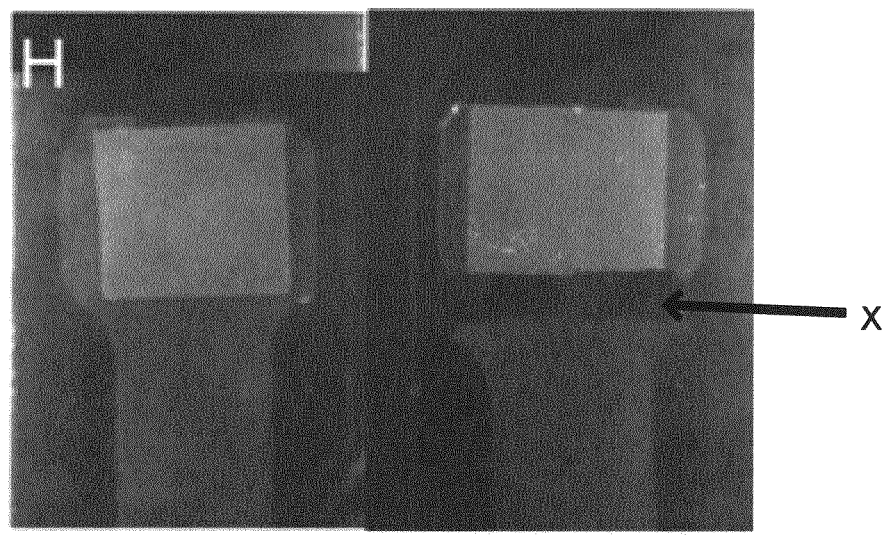
FIGS. 9a and 9b show photographs of a polypropylene (PP) mesh-incorporated scaffold and a collagen mesh incorporated scaffold, respectively, before and after having been subjected to a tensile force.

When samples were subjected to a tensile force, the polypropylene (PP) mesh-incorporated scaffold ruptured X at the interface of collagen and PP mesh, indicating a localized weakness., see FIG. 9a.

Figure 9B:
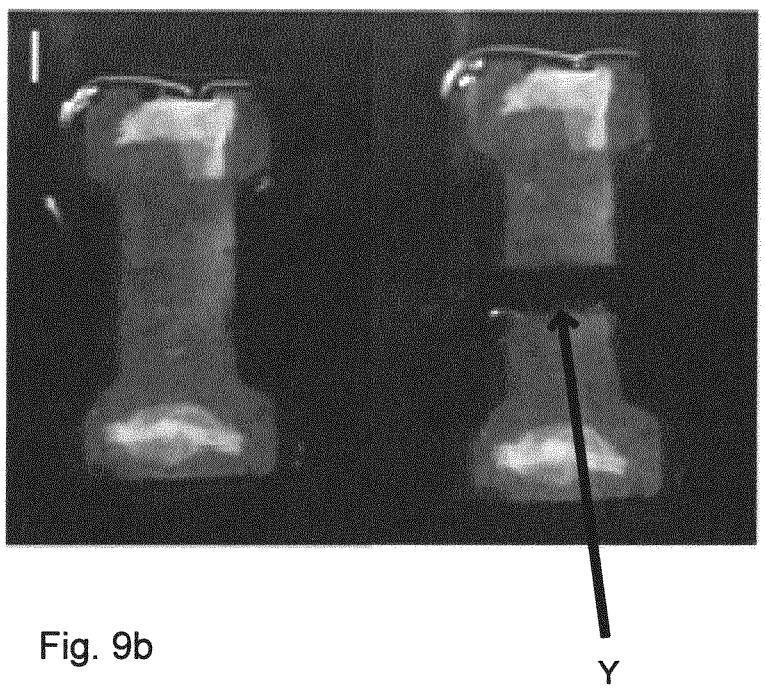

Samples with a crosslinked collagen network 4 in the center and peripheral region composed of the composite material comprising a collagen mesh, the tensile force was transferred to the center of the test specimen that was comprised of the crosslinked collagen 4 only where the hydrogel was weaker than the tabs and ultimately ruptured Y, see FIG. 9b.

Figures 10A, 10B:
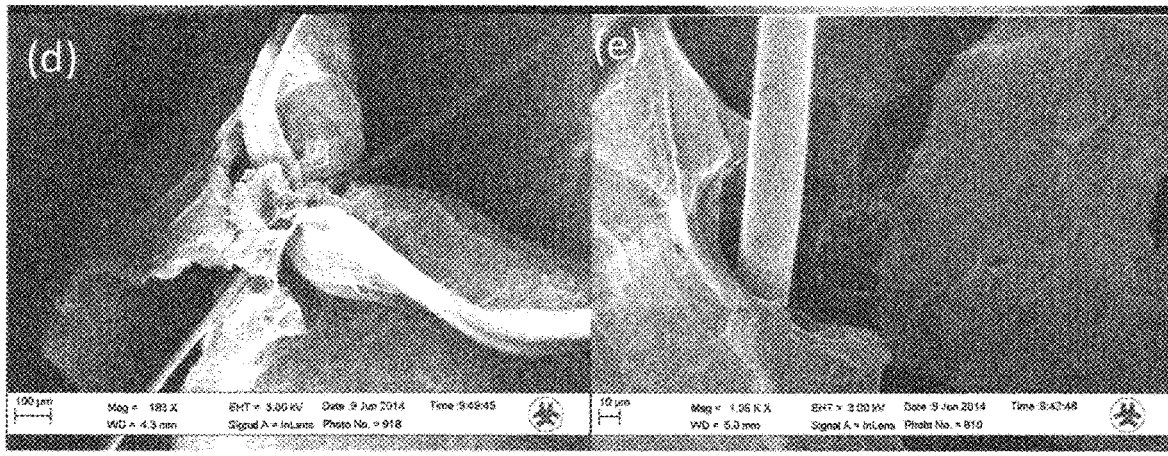
FIGS. 10a and 10b show the suturability of bioengineered implants with collagen mesh in the skirt and control implants without such collagen mesh, respectively.

The suturability of the implants comprising a crosslinked collagen network 4 in the center and peripheral region composed of the composite material comprising a collagen mesh were tested by suturing them onto explanted pig eyes. As shown in the SEM images in FIG. 10a, the implants held sutures and did not tear while the control implants FIG. 10b (crosslinked collagen network without collagen mesh) did not hold all the sutures and were not as good as the composite collagen hydrogel material-containing implants.

Collagenase Degradation

To evaluate in vitro degradation rate of biomaterials, collagenase Type I (from Clostridium histolyticum) was used. Briefly, 80 mg samples (150 μm thick) of the crosslinked collagen network, and composite collagen hydrogel material were incubated in collagenase-buffer solution. The hydrogels were weighed at different time points after the surface water was gently blotted away (0, 1, 2, 3, 6, 8, 10, 14, 16, 18 hours). The percent residual mass of hydrogels was calculated according to the ratio of the weight at each time point to the initial hydrogel weight at time zero.

Figure 11:
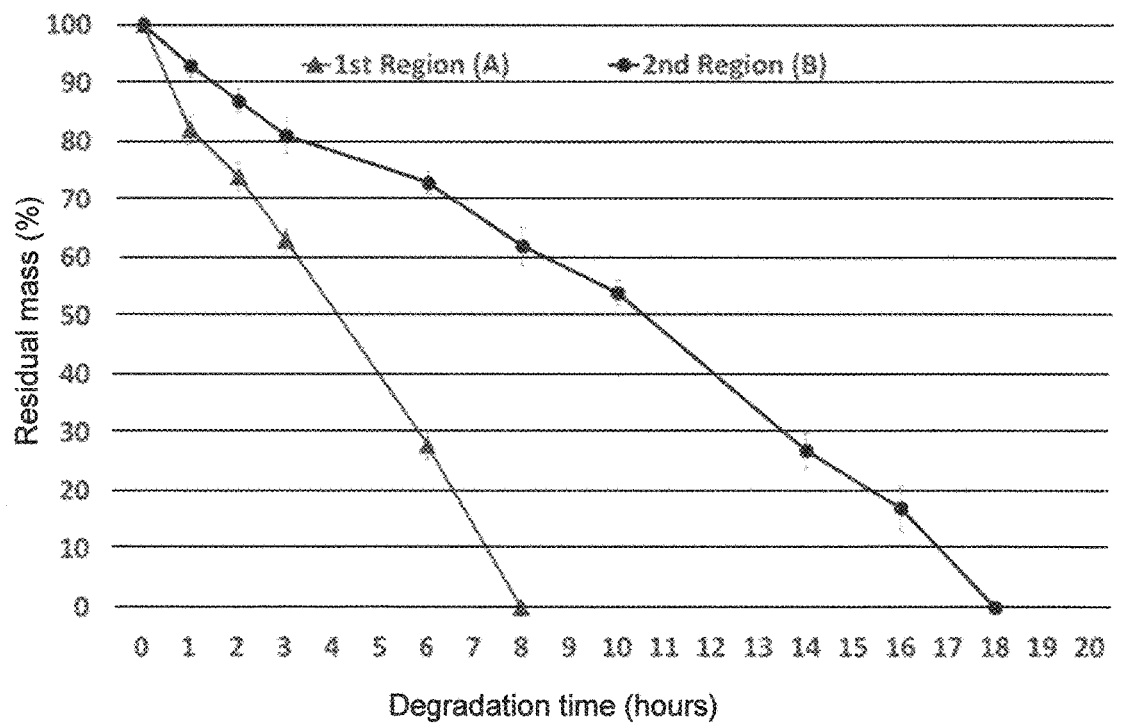
FIG. 11 is a graph showing the degradation time in vitro for different materials.

In the in vitro collagenase assay, composite materials (first region A) were less resistant toward collagenase degradation than crosslinked collagen network (second region B), see FIG. 11. The crosslinked collagen network degraded by 50% in vitro in 11 hours, while the composite material took only 4 hours to degrade by 50% in vitro due to less degree of cross-linking in this material.

Hence, an implantable ophtalmic device shows a higher degree of degradation in the regions with composite material than in the regions with crosslinked collagen network.

Evaluation of Human Corneal Epithelial Cell Growth

Immortalized human corneal epithelial cells (HCECs) (American Type Culture Collection, ATCC, Manassas, USA) were used to evaluate cell biocompatibility of the materials. HCECs were seeded in wells within a 96-well cell culture plate without the hydrogels (control), on top of 150 mm$^2$ pieces of composite collagen hydrogel material, or composite-PP mesh and crosslinked collagen networks and then supplemented with a serum-free medium optimized for the culture of human corneal epithelial cells (EpiGRO™ Human Ocular Epithelia Complete Media Kit, Millipore, Billerica, Mass., USA). Once the control wells became confluent, after approximately 3 days of culture, all wells were stained with the LIVE/DEAD® Viability/Cytotoxicity assay (Invitrogen). Stained cells were photographed with a Zeiss inverted fluorescent microscope using the Zen software (Zeiss LSM700) under a 10× magnification on day 5 post-seeding. Green and red fluorescence corresponded to live and dead cells, respectively.

The composite collagen hydrogel material supported growth and proliferation of HCECs, while cells did not appear to populate composite-polypropylene mesh. The composite collagen hydrogel material and crosslinked collagen network equally supported the cell growth and proliferation very similar to the positive control petri dish surface (not shown).

Animals and Femtosecond Laser-assisted Intrastromal Keratoplasty (FLISK)

With approval by the Linköping Animal Research Ethics Committee (Application no. 108-12) and following the Association for Research in Vision and Ophthalmology (ARVO) guidelines for the Use of Animals in Ophthalmic and Vision Research, 10 male New Zealand white albino rabbits weighing 3-3.5 kg were operated. Surgery was performed under general anesthesia with intramuscular injection of 25 mg/kg ketamine (Ketalar 50 mg/ml; Parke-Davis, Taby, Sweden) and 5 mg/kg xylazine (Rompun 20 mg/ml; Bayer, Gothenburg, Sweden). Local anesthetic drops were also used (tetracaine hydrochloride eye drops 1%, Chauvin Pharmaceuticals Ltd., Surrey, UK). The right eye underwent intra-stromal corneal transplantation in all 25 rabbits while left eyes served as untouched negative controls. Operations were performed according to the technique of femtosecond laser-assisted intra-stromal keratoplasty (FLISK). An Intralase iFS 150 kHz femtosecond laser (Abbott Medical Optics, Solna, Sweden) was used to cut corneal buttons of purely stromal tissue (not including any part of the epithelium or endothelium). The precise dimensions and location of the buttons to be removed were pre-programmed via the laser's user interface and were identical for all rabbits. For the current study, 3 mm diameter buttons of 150 μm thick native tissue were removed from a mid-stromal depth (125 μm depth from the corneal surface to the anterior surface of the excised button). In all groups, femtosecond laser-cut buttons were manually excised using surgical forceps (through an arc-shaped opening to the corneal surface limited to 70° of the circumference, leaving an empty stromal pocket. Immediately prior to implantation of the biomaterials, a 3 mm diameter tissue trephine was used to cut circular buttons from 150 μm thick flat sheets of the biomaterial, the implantable ophthalmic device comprising composite collagen hydrogel material in the periphery, skirt, of the device and crosslinked collagen network in the center, core. The core and skirt regions were clearly visible (due to difference in core and skirt transparency) and were deemed viable for in vivo implantation and tracking. Rabbits were divided into 2 groups. In the first (positive control) group, native corneal tissue was cut intra-stromally with a femtosecond laser, excised and thereafter manually inserted again in its former position into the empty stromal pocket using anatomical forceps (autograft transplantation). In the second group, the FLISK method was identical except that the excised corneal tissue was replaced by the bioengineered implantable ophthalmic device. No postsurgical sutures were used because the intra-stromal location and small access cut were sufficient to ensure implants remained in place within the host stromal pocket. After surgery and for the first postoperative day, all operated eyes received antibiotic eye ointment (Fucithalmic 1%, Leo Pharmaceuticals, Denmark) three times daily. The use of steroids (Opnol eye drops 1 mg/mL, CCS Healthcare AB, Borlänge) was minimal and restricted to severely inflamed eyes following operation.

All FLISK procedures were performed without intraoperative complications. Native midstromal tissue was extracted and replaced with either the biomaterial or the same extracted tissue (autograft).

Postoperative Clinical Evaluation

Evaluation of intra-stromal location of implants and corneal thickness measurement was performed by Anterior Segment Optical Coherence Tomography (AS-OCT; Visante OCT, Carl Zeiss AB, Stockholm, Sweden) in high resolution mode (average of three thickness measurements per cornea). Immediately after operation, AS-OCT examination confirmed the intrastromal presence of implants and absence of corneal perforation and revealed variable swelling of the corneas that subsided after 1 month and fully stabilized after 3 months, while three months after implantation, all implants were retained, and implant materials remained transparent.

Figure 12:
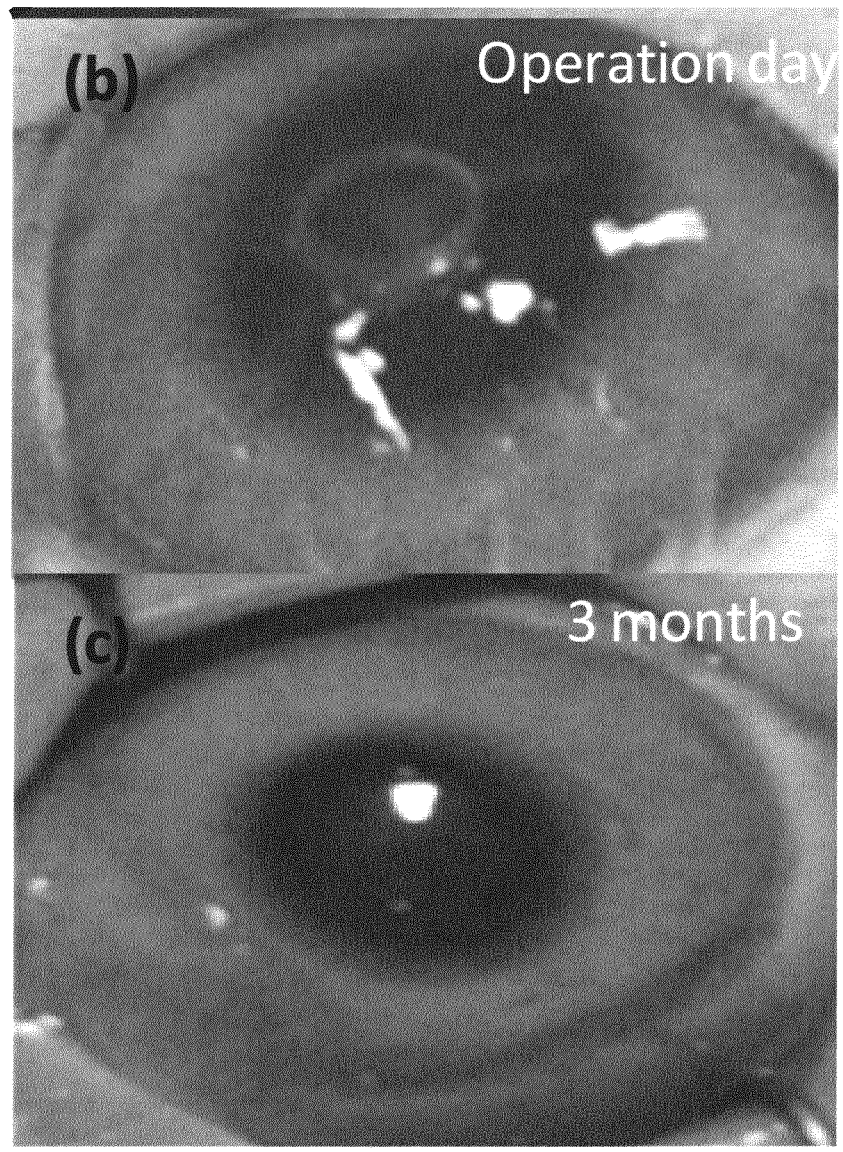
FIG. 12 shows photographs of an implanted ophthalmic device in rabbit corneas on the operation day and three months after operation.
Figure 13:
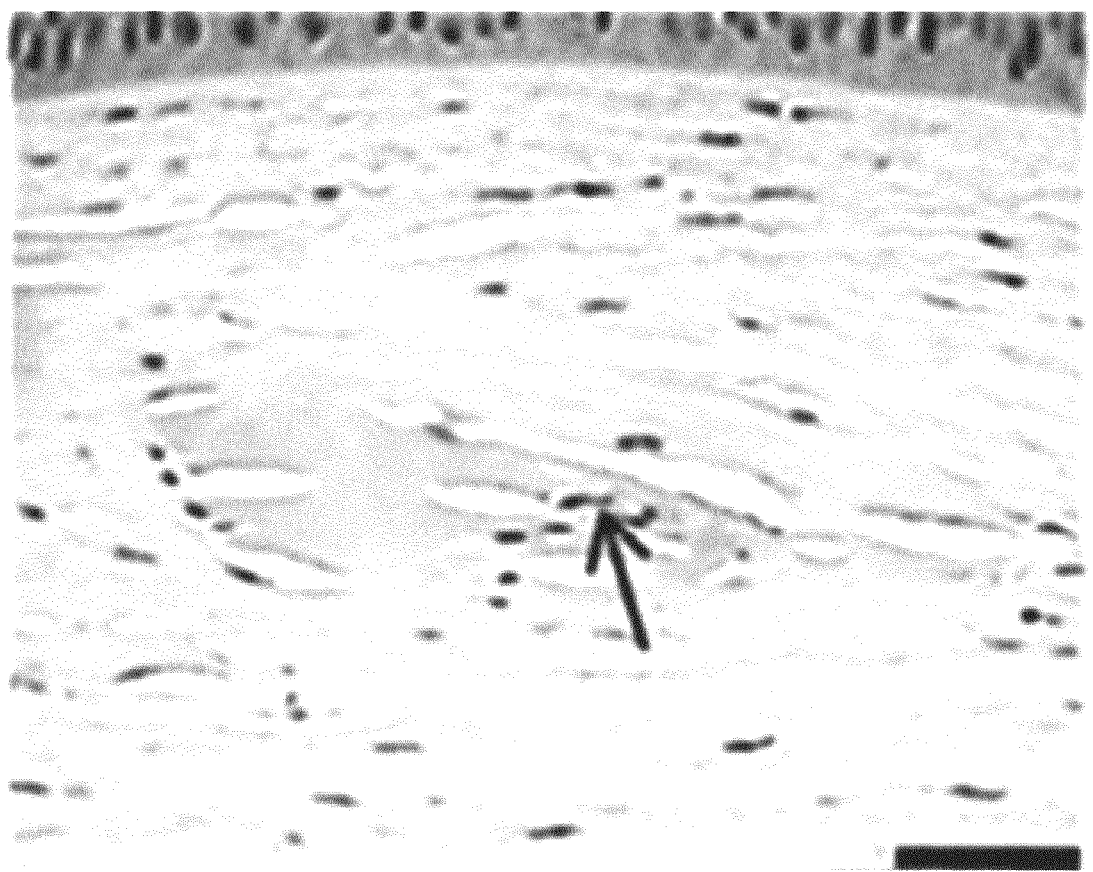
FIG. 13 shows a photograph three months after implantation of a peripheral region, skirt, of an implant being invaded by stromal cells.

The implants were studied for 3 months in vivo in the rabbit cornea during which they were retained and were stable with no adverse effects. The transparent core and the semi-transparent skirt could be visualized by photography, see FIG. 12, on the operation day and three months after operation. (Corneas were photographed with a high-magnification digital camera (Nikon D90 camera, Nikon Canada Inc., Toronto, Canada). No inflammation or vascularization of implants was observed, despite the absence of postoperative steroid treatment. Three months after implantation, both the skirt and the transparent biomaterial core were barely visible. The skirt region was invaded by stromal cells, see FIG. 13 (the black arrow indicate cells within the implant), and stromal nerve invasion of implants was observed. Additionally, the skirt section slowly degraded over time as expected while restoring the morphologic and physiologic corneal milieu. After three moths the implant had an intact core region and partial remnant of the skirt. Fibroblast activity within the femtosecond laser cut diminished, and permitted sub-epithelial nerves to traverse the circular cut. At three months, all implanted corneas remained transparent in vivo. The rabbits were sacrificed after 3 months.

Histopathological Evaluation

The rabbit corneas with the implants were explanted, fixed and were imbedded in paraffin and sectioned to 4 µm-thickness and hematoxylin and eosin (H&E) staining was performed. For immunohistochemical analysis, sections from paraffin-embedded tissues were deparaffinized, trypsinized and endogenous peroxidase was blocked. Sections were incubated with the following primary antibodies for 30 minutes: mouse monoclonal anti-alpha smooth muscle actin, α-SMA (dilution 1:25, ab 7817, Abcam, Cambridge, United Kingdom), mouse monoclonal anti-type III collagen (dilution 1:100, Acris AF 5810, Germany), mouse monoclonal anti-leukocyte common antigen CD45 (dilution 1:400, Acris AM02304PU-S, Germany). After antibody application and incubation in envision HRP, DAB liquid chromogen was applied to all samples and sections were counterstained with hematoxylin. Samples were dehydrated, cleared in xylene and coverslipped with Mountex mounting medium (Histolab Products AB, Gothenburg, Sweden). In all cases, control samples were used and omission of the primary antibody eliminated specific staining. Light microscopy was performed with an Axiophot Photomicroscope (Zeiss, West Germany) under 10× and 20× magnification.

Scanning and Transmission Electron Microscopy

Scanning Electron Microscopy (SEM) was Performed Using a ZEISS (LEO 1550 Gemini) field emission microscope. The biomaterial samples were prepared via immersion in liquid nitrogen for 60 s followed by lyophilization for 24 hours. Samples were sputtered with a 2 nm gold coating prior to mounting for SEM. Samples were examined using an accelerating voltage of 3 KeV and a working distance of 3-5.5 mm.

Figure 5:
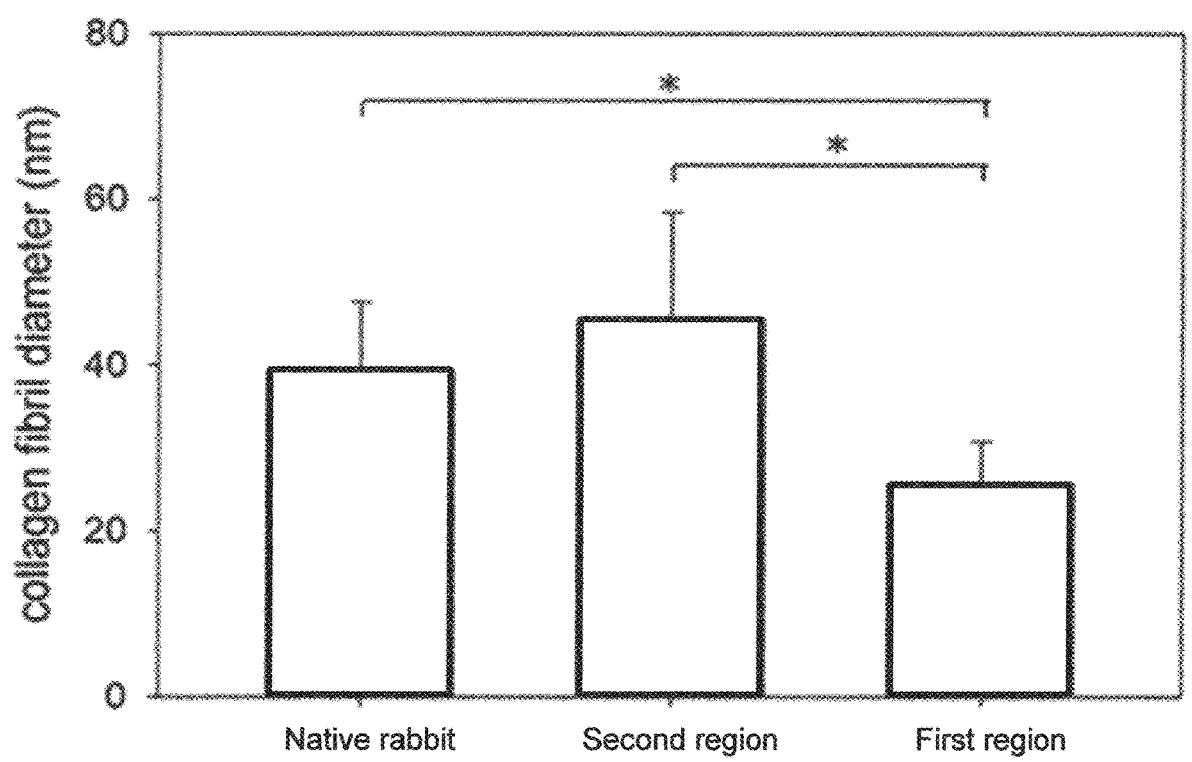
FIG. 5 shows the size of collagen fibrils in different regions of the device in FIG. 1 compared to those in native rabbit stroma.

For Transmission Electron Microscopy (TEM), fixed samples were imbedded in resin (Epon 812; TAAB, Reading, England). 4 µm thick sections were made and stained with toluidine blue dye for light microscopy in order to specify the area of interest. Ultrathin sections of 60 nm were cut from the polymerized block and these sections were collected on 200 mesh copper grids. Finally, the ultrathin sections were stained with uranyl and lead citrate and imaged with a transmission electron microscope (EM JEM 1230, JEOL Ltd., Tokyo, Japan). TEM images were utilized for the quantification of collagen fibril diameter. Images depicting different regions were used for collagen fibril diameter measurements in the native corneal stroma, central core and peripheral skirt region (3 images for each). For core and skirt parts, TEM pictures prior to implantation were analyzed. From each image, the diameter of 30 different collagen fibrils was measured as shown in FIG. 5.

Statistical Analysis

Thickness of implanted materials measured by OCT was compared using one-way analysis of variance (ANOVA). Change in corneal thickness in the same eyes relative to immediately postoperative and to the final examination was analyzed by the paired t-test. Subbasal nerve density across groups at 3 months postoperatively was compared using one-way ANOVA. Collagen fibril diameter measurements were compared Kruskal-Wallis one-way ANOVA on ranks with Dunn's method to isolate pairwise differences. For all statistical tests, two-tailed significance below 0.05 was considered significant, and all tests were performed with Sigma Stat 3.5 software (Systat Software Inc., Chicago, Ill., USA).

Nerve Status

IVCM examination revealed coverage of all implanted corneas by epithelium postoperatively. The corneal epithelium derives innervation from the subbasal nerve plexus, which was visualized by IVCM. No significant difference in subbasal nerve density was found between native rabbit cornea, biomaterial or autografts at three months, and nerve morphology appeared normal with thin nerve fibers running roughly parallel.

Stromal Cell Migration Following Implantation

Corneal examination at the cellular level was conducted in vivo by IVCM, and ex vivo by H&E and immunohistochemical staining. IVCM of core-skirt peripheral interfaces revealed round or oval-shaped reflective cells with dark nucleus at one and three months, in close proximity to visible skirt remnants. This cell morphology corresponds to mature macrophages, which were also found in autografts. The central implanted region in autografts was populated by stromal keratocytes while in biomaterials, sparse keratocyte-like and macrophage-like cells were observed within the implant material. Histochemical staining confirmed that initially acellular implants were populated with host cells at three months. Cells were found in both core and in remnants of the skirt, and consisted of $\alpha$-SMA+ myofibroblasts originating from activated keratocytes and/or CD45+ bone marrow-derived cells such as macrophages. Although inflammatory cells were observed in vivo and ex vivo, no signs of inflammation were noted upon clinical examination of implanted eyes at three months.

Twenty-nine types of collagens have been identified, but types I, II and III are the most abundant and make up the majority of the extracellular matrix macromolecules and have several roles. For instance, over 90% of the collagen in the human body is type I. The above described composite collagen hydrogel material is applicable to all fibril-forming collagens (e.g. types I, II, III, V, XI, etc.). This is because many of the crosslinking sites that are needed for formation of crosslink networks are common among these collagens. In addition, these collagens are protein complexes whose basic units consist of the same triple helices (tropocollagen) in which three polypeptide chains are wound around each other like a piece of rope. Collagen molecules can self-assemble into micro-fibrils and then fibrils.

For tissue engineering applications, one collagen type or a combination of various types can be used depending on the target tissue or organ that need to be replaced or repaired. For example, collagen type I is abundant in the human cornea, skin, tendon, and bone while collagen type II is abundant in cartilage and type III is abundant in veins Collagen type III is more abundant in skin, lung, cornea, and the vascular system, frequently in association with type I collagen.

The invention claimed is:

1. A composite collagen hydrogel material comprising:
   a first collagen network comprising collagen crosslinked with a first crosslinking agent,
   a second collagen network comprising collagen crosslinked with a second crosslinking agent, and
   a non-crosslinked collagen mesh comprising partially and plastically compressed collagen hydrogel with a compression degree of 50-95%,
   wherein the first crosslinking agent and the second crosslinking agent are different,
   wherein the collagen mesh is embedded in the first collagen network and/or second collagen network, and
   the first collagen network, the second collagen network and the collagen mesh are physically and chemically interconnected in the composite collagen hydrogel material,
   wherein the composite collagen hydrogel material has a light transmission of at least 80% at 550 nm,
   wherein the collagens are a fibril-forming collagens and wherein the constituents of the composite collagen hydrogel material, the first collagen network, the second collagen network and the collagen mesh, form a merged composite material without distinct interfaces between the constituents.

2. The composite collagen hydrogel material of claim 1, wherein the plastically compressed collagen hydrogel has a partial compression degree of 55-90%.

3. The composite collagen hydrogel material of claim 1, wherein the collagen of the first and/or second collagen network and the collagen mesh is Type I collagen.

4. The composite collagen hydrogel material of claim 1, wherein the first and/or second collagen network and the collagen mesh comprises the same type of collagen.

5. The composite collagen hydrogel material of claim 1, wherein the collagen content in the first and/or second collagen network is 1-50%.

6. The composite collagen hydrogel material of claim 1, wherein the first and/or second crosslinking agent is a non-polymeric short range carbodiimide crosslinking agent.

7. The composite collagen hydrogel material of claim 1, wherein the first and/or second crosslinking agent is a polymeric long-range amine-type multi-functional crosslinking agent comprising amine-type multifunctional crosslinkers from the polyethylene glycol (PEG) family, selected from a group comprising PEG Succinimidyl ester (NHS-PEG-NHS) Multi-arm PEG Succinimidyl NHS ester, poly (ethylene glycol) dialdehyde (PEG-DA), polyethylene glycol dibutylaldehyde, polyethylene glycol diacrylate and combinations thereof.

8. The composite collagen hydrogel material of claim 1, wherein the pH of the first and/or second collagen network is acidic, pH 3-6, and the pH of the collagen mesh is neutral, about pH 7.

9. The composite collagen hydrogel material of claim 1, wherein a ratio of the first crosslinked collagen network to the second crosslinked collagen network in the composite collagen hydrogel material is 1:1 to 100:1.

10. The composite collagen hydrogel material of claim 1, wherein the molar ratio of the first crosslinking agent to collagen in the first crosslinked collagen network is 0.5:1 to 3:1.

11. The composite collagen hydrogel material of claim 1, wherein the molar ratio of the second crosslinking agent to collagen in the second crosslinked collagen network is 0.1:1 to 2:1.

12. The composite collagen hydrogel material of claim 1, wherein the collagen content of the collagen mesh is 0.1-20%.

13. The composite collagen hydrogel material of claim 1, wherein the ratio of the collagen content in the collagen mesh to the collagen content in the first and/or second collagen network is 1:50.

14. The composite collagen hydrogel material of claim 1, wherein the collagen mesh is loaded with cells, tissue factors, growth factors, bioactive agents, and/or drugs.

15. An ophthalmic device comprising the composite collagen hydrogel material of claim 1.

16. An implantable ophthalmic device comprising:
   a first and a second region, wherein
   the first region comprises the composite collagen hydrogel material of claim 1, and
   the second region comprises an essentially transparent crosslinked collagen hydrogel comprising the same first and/or second crosslinked collagen networks as the composite hydrogel material,
   wherein the first and second regions are interconnected regions connected through the first and/or second crosslinked collagen networks.

17. The implantable ophthalmic device of claim 16, wherein the device is a corneal onlay, corneal inlay, or full-thickness corneal implant.

18. The implantable ophthalmic device of claim 16, wherein the first region is positioned in a peripheral area of the device.

\* \* \* \* \*